United States Patent
Boche et al.

(10) Patent No.: US 6,296,648 B1
(45) Date of Patent: Oct. 2, 2001

(54) SUTURING AID

(75) Inventors: Hartmut Boche, Immenstaad; Hans Scherieble, Esslingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/180,634

(22) PCT Filed: May 8, 1997

(86) PCT No.: PCT/EP97/02365

§ 371 Date: May 3, 1999

§ 102(e) Date: May 3, 1999

(87) PCT Pub. No.: WO97/42880

PCT Pub. Date: Nov. 20, 1997

(30) Foreign Application Priority Data

May 10, 1996 (DE) ............................................ 196 18 885
Aug. 31, 1996 (DE) ............................................ 196 35 354

(51) Int. Cl.[7] .................................................. A61B 17/04
(52) U.S. Cl. ............................................................ 606/148
(58) Field of Search ................................. 606/148, 144, 606/139, 169, 213, 153, 201, 216, 218; 600/204, 210, 214, 190, 215, 219; 81/314, 315, 316, 341, 345

(56) References Cited

U.S. PATENT DOCUMENTS

| | | |
|---|---|---|
| 4,836,205 | 6/1989 | Barrett . |
| 5,176,128 | 1/1993 | Andrese . |
| 5,351,679 | 10/1994 | Mayzels et al. . |
| 5,364,408 * | 11/1994 | Gordon ................................ 606/144 |
| 5,391,182 | 2/1995 | Chin . |
| 5,474,568 | 12/1995 | Scott . |
| 5,507,755 | 4/1996 | Gresl et al. . |
| 5,573,495 * | 11/1996 | Adler .................................. 600/204 |

FOREIGN PATENT DOCUMENTS

| | | |
|---|---|---|
| 640126 * | 12/1936 | (DE) . |
| 40 21 153 A1 | 1/1992 | (DE) . |
| 42 10 724 C1 | 7/1993 | (DE) . |
| 44 15 521 A1 | 11/1995 | (DE) . |
| 196 35 354 A1 | 11/1997 | (DE) . |

* cited by examiner

Primary Examiner—Henry J. Recla
Assistant Examiner—Vy Q. Bui
(74) Attorney, Agent, or Firm—St. Onge Steward Johnston & Reens LLC

(57) ABSTRACT

A suturing aid for closing minilaparotomies from minimal-invasive surgical operations comprises a shaft whose distal end is provided with at least one plane support that can be swung out laterally. An actuating element serves for swinging out the support, whereby the support can be moved between a first working position, in which it is folded up towards the proximal end, a second position, in which it is folded out laterally and a third working position, in which it is folded out towards the distal end of said shaft.

19 Claims, 9 Drawing Sheets

SUTURING AID

The present invention relates to a suturing aid for closing minilaparotomies from minimal-invasive surgical operations.

Minimal-invasive surgery has become widely accepted in recent times. Especially laparoscopic operations are almost exclusively carried out by minimal-invasive surgery techniques, due to their outstanding advantages for both, patient and surgeon.

In the case of this operating technique guide sleeves, also known as trocar sleeves, which accommodate a pointed mandrel, also known as trocar mandrel, are introduced, for example, into the abdominal cavity through the abdominal wall. After the trocar mandrel has been pulled off, it is then possible to insert endoscopes and surgical instruments through the sleeve into the operating area. In complicated operations, more than one trocars can be introduced at different points. The surgeon can then perform the operation under visual control, in the abdominal cavity that has been opened only through small punctures.

Upon completion of the operation, the instruments and, thereafter, the trocar sleeve are removed. The remaining wounds, known as minilaparotomies, are small, but penetrate the entire abdominal wall, i.e. the skin, the hypodermis and the muscular coat, the muscles and the peritoneum.

Initially, one used to let the minilaparotomies remaining with that operation technique unclosed, but this led to the formation of hernia, sometimes combined with visceral or enteric encarceration, comparable with inguinal hernia, umbilical hernia or postoperative hernia. One therefore developed instruments with the aid of which minilaparotomies can be closed.

An instrument for closing trocar wounds is known from U.S. Pat. No. 5,474,568.

This instrument comprises a long shaft that carries a scissors-like handle on its proximal end. In the area of the distal end, there are provided needles that carry a thread and that are bent to an approximately semicircular shape and can be swung out laterally. The long thin shaft is pushed through the trocar wound, with the needles in the retracted position in which they do not radially project beyond the contour of the shaft. Once introduced into the body, the needles are extended laterally and penetrate into the abdominal wall from its bottom surface, pulling the thread with them, until the point of the curved needle reaches and engages the shaft body. During the returning motion, the curved needle body as such is detached from the engaged point, and the thread held by it. The device is then pulled off, and the thread is knotted.

Thus, this instrument works as a true suturing device.

It is a disadvantage of that device that the surgeon does not know the moment when the shaft or its distal area has just penetrated the entire abdominal wall, but has not yet entered any other organs located below the abdominal wall. one must realize in this connection that once the trocar sleeve has been pulled off, it is no longer possible to visually observe and control the suturing process in the body.

A similar suturing device, comprising curved needles or needle holders that can be swung out laterally, is known from U.S. Pat. No. 5,364,408.

DE-C-4 210 724 describes a surgical actuating device having an elongated shaft portion from which spreading elements can be laterally extended in a plane vertical to the shaft axis. The motion of the spreading elements, that can be extended in a radial plane, is effected by rotation of a shaft extending through the shaft portion. According to one embodiment it is provided to arrange on the outer points of the spreading elements upright needles capable of penetrating through the abdominal wall. This device again works as a suturing device and provides the risk that surrounding organs may get damaged by the radial movement in a radial plane.

An organ manipulator known from DE-A-4 021 153 comprises a spreading body consisting of a multi-joint lever system with articulated arms that are pivotally connected one with the other, for being moved between an elongated position, in which it can be introduced into the body cavity, and an expanded position, where the arms form together a triangular flat shape. This organ manipulator serves exclusively the purpose to expose organs inside a body cavity.

So, to this day, the problem of closing minilaparotomies has not been technically solved in a satisfactory way.

Due to the small incision in the skin, with a diameter in the range of approximately 10 to 15 mm, and the thickness of the abdominal walls, which is in the range of several centimeters, the operator has poor control of all layers of the abdominal wall that have to be closed. Closing the layers of an abdominal wall, without visual inspection, with the aid of thread and needle or special clips, is very risky and would be irresponsible because of the existing risk of damage.

Now, it is the object of the present invention to provide an auxiliary device for closing minilaparotomies that makes it easier for the surgeon to apply a suture and that prevents damage during the closing of minilaparotomies.

The invention solves this object by a suturing aid having a shaft whose distal end is provided with at least one plane support, that can be swung out laterally, and an actuating element for swinging out the support, whereby the support can be moved between a working position in which it is folded up towards the proximal end, a working position in which it is folded out laterally, and a working position in which it is folded down towards the distal end.

The term "plane support" as used in the context of the present invention is meant to describe any two-dimensional structure either resembling a plate, or in the form of a plate, or in the form of a grid or grate, which ultimately can be applied flat against the bottom face of an abdominal wall. The term "plane" includes slightly curved surfaces or waved surfaces.

The term "support" not only means that something, for example the suturing device as such, can be placed upon that surface, but also means that the support can be placed against a part of a body.

The term "swinging out laterally" as used in the context of the present invention means that the support can be moved in outward direction, or folded out laterally, with respect to the longitudinal axis of the shaft.

The term "working position in which it is folded up towards the proximal end" is meant to describe a position of the support in which the free outer end of the support is closer to the proximal end than its axis of rotation, viewed from the distal end towards the proximal end along the shaft axis.

The term "working position in which it is folded out laterally" is meant to describe a position of the support in which its plane forms an angle of approximately 90° with the shaft axis.

The term "working position in which it is folded down towards the distal end" is meant to describe a tilted position in which the support has been pivoted by more than 90° relative to the working position mentioned first, being folded up towards the proximal end, i.e. in which its outer end, viewed from the distal towards the proximal end, is positioned below its axis of rotation.

Due to this arrangement, it is now possible to fold the support up into a position in which it closely rests against the shaft, so that the shaft and support assembly can be introduced through the minilaparotomy in a way similar to the point of an arrow. As long as the support remains inside the wound channel, that leads through the abdominal wall, it cannot be swung out laterally, which can be recognized by the surgeon simply by the fact that the actuating element, which serves to swing out the support, cannot be moved.

When the support has penetrated for example the abdominal wall, the uppermost folded up end of the support is the last element of the support to leave the wound channel. Once this position has been reached, the support can be swung out relative to the shaft from the bottom face of the abdominal wall towards the interior of the body. This safely prevents, on the one hand, any parts of the body from being caught between the lower face of the abdominal wall and the support; rather, the contrary effect can be achieved, namely that the swinging movement, away from the lower face of the abdominal wall and towards the interior of the body, acts to urge away any organs from the lower face of the abdominal wall that is to be sutured. The easy movement is felt by the surgeon immediately after the uppermost folded-up end of the support has left the wound channel, because it is now possible for him to operate the actuating element without any effort in order to actuate or swing out the support. So, the surgeon knows for sure, without visual control, when the suturing aid has been pushed through the wound channel a sufficient length.

Now, when the support is moved into its laterally folded-out defined working position, the suturing aid can be moved a little away from the body in this position, whereby the support is caused to apply itself flat against the lower face of the abdominal wall or the tissue area through which the wound channel extends. As a result of this lifting motion, the tissue layer to be sutured can be lifted off any underlying organs, for example when suturing an abdominal wall, from the viscera. It is now possible to introduce needle and thread from the outside along the shaft until they hit upon the support. For example, if the surgeon uses a so-called Dechamps hook, which resembles the shape of a corkscrew, then he can wind that tool through the wound channel along the shaft of the suturing aid until its point hits upon the support. The hook, which also carries the thread, can then be driven through the abdominal wall from below in a manner such that the suture is applied at the desired point. It is thus ensured, without any visual control, that the Dechamps hook, or another needle hook, will not penetrate into the body excessively deep and will not by error attach an inner organ to the lower face of the abdominal wall. The suturing aid, therefore, does not work as a suturing device as such, but merely acts to aid and support a known suturing device, for example in applying a suture with the aid of a Dechamps hook.

Once the thread has been applied, and the needle or the Dechamps hook has been pulled off, the suturing aid can be pulled off, for which purpose the support is folded down towards the distal end, i.e. towards the interior of the body.

This folding-down motion provides the considerable advantage that instead of being "folded back" to the turned-up position—in which there is a risk that tissue parts or possibly the thread or other elements may get caught between the folded-up support and the shaft—the swinging movement is directed away from the lower face of the tissue to be sutured. The lifting and pulling-off movement of the shaft, and the swinging movement towards the distal end may take place synchronously so that immediately before the suturing aid is pulled off, part of it, namely the section of the support in the area of its connection to the shaft, is pulled into the wound channel so that only a relatively small portion of the support is moved away from the abdominal wall and into the interior of the body, whereby any risk of damage is excluded. This swinging movement has the effect to move any parts of the body in the vicinity of the support away from the bottom face of the tissue layer to be sutured, thereby excluding the risk that some portion or other may be pulled inadvertently into the wound channel.

In summary, this permits the surgeon to apply a suture at an exactly defined point and without any impairment of surrounding organs, without exact visual control. The process does not require the concentrated attention of an experienced surgeon, but may instead by carried out also by less experienced or trained persons.

The lifting action described above, with the support folded-out laterally, not only permits the layer, for example the abdominal wall, to be lifted off any neighboring organs, but also has the effect to slightly spread the wound channel so that parts of the plane of the support can be recognized from the outside which enables the tool, for example a Dechamps hook, to be used with particular ease.

The object is entirely achieved in this manner.

According to a special embodiment of the invention, the support comprises two diametrically opposite vanes.

This feature now provides the advantage that by providing the two vanes, plane supports are created on both sides of the shaft so that a suture can be applied, for example, at the left and right of the shaft, which may already suffice to close a minilaparotomy. During introduction, the two vanes form a "V" similar to the point of an arrow, with the open end of the V pointing in downward direction during the pulling-off motion. This fact, namely that the open end of the V points in downward direction during the pulling-off motion, ensures that no tissue portions will be caught and entrained while pulling off the unit.

In a further embodiment of the invention, the actuating element is configured as a rod, which is arranged to slide along the shaft and is hinged, on the distal end, on the support, with the axis of the hinge forming the pivot axis of the support.

This feature provides on the one hand the constructional advantage that the unit requires only a small number of simple and, consequently, easy to clean components which ultimately results in an extremely narrow design of the suturing aid.

In a further embodiment of the invention, the support is hinged, at a certain distance from its pivot axis, on one end of an actuating lever whose other end is hinged on the shaft.

This feature provides the advantage that due to the lever arrangement the axial displacement of the actuating element along the shaft is precisely translated into the desired pivotal movement of the support.

In still another embodiment of the invention, the distance between the pivot axis of the support and the connection point of the lever corresponds to approximately one third of the overall length of the support.

This lever geometry permits the displacing movement of the actuating element to be converted, in a functionally safe way and without much effort, into the pivotal movement of the support.

In another embodiment of the invention, at least one guide for a suturing tool is provided on the side of the support facing the proximal end of the suturing aid.

This feature provides the advantage that the suturing tool, once it has reached the surface of the support, can be moved a little to and from until it enters the guide, for example a guide groove. This is felt by the surgeon who then knows that the suturing tool now occupies a given position on the support, This allows him to place the suturing tool precisely in the position to the sutured, and to apply the thread exactly, without visual control of the tip of the suturing tool.

In a further embodiment of the invention, the actuating element is protected against torsion inside the shaft.

This feature provides the advantage that the actuating element remains in an exactly defined angular position relative to the shaft so that the surgeon is aware of the position and/or the extension of the support even after the latter has been introduced into the body so that it cannot be seen any more by the surgeon.

In a further embodiment of the invention the actuating element is biased by a spring in such a way that the support is moved automatically from its working position in which it is folded up towards the proximal end into its laterally folded-out working position.

This extremely preferred embodiment provides the substantial advantage that once the support has been pushed through the wound channel, it will automatically fold out laterally, whereby the actuating element is moved as well. This can be recognized by the surgeon from the outside and tells him exactly that he has pushed the support fully through the wound channel. This prevents the suturing aid in an especially simple way from being driven in too far by mistake.

In a further embodiment of the invention, the spring force is adjusted in such a way that the working support will be folded out laterally only to an intermediate position somewhat before the working position in which the support is fully folded out laterally.

This feature provides the advantage that the surgeon, once he has recognized that the folded-up support has passed the wound channel, can pull the suturing aid slightly back to bring the support into the desired working position, i.e. mostly into the position in which it is folded out laterally by exactly 90°, in which it can then be fixed.

In a further embodiment of the invention, orientation marks are provided on the shaft and/or on the actuating element that indicate the angular position which the working support occupies at any time.

This feature now provides the advantage that the relative position between the shaft and the actuating element, which can be moved relative to the shaft, tells the surgeon at any time, and without any visual contact to the support, what angular position is occupied by the support at any time. This contributes very much towards improving the handling safety of the suturing aid.

In a further embodiment of the invention, a fixing mechanism is provided by means of which the working support can be locked in given angular positions.

This feature provides the advantage that the support can be fixed by the fixing mechanism especially in its laterally folded-out working position so that thereafter any further manipulation, such as introduction and application of the thread by means of a Dechamps hook, can be carried out without any change in relative position between the support and the shaft.

In a further embodiment of the invention the fixing mechanism is configured as a spring lever, pivoted on the shaft, which comprises a locking element arranged to engage corresponding recesses provided on the actuating element.

This feature not only provides the advantage that the fixing mechanism can be actuated, i.e. closed or released, in an easy fashion, but tells the operator at the same time in which position it is being fixed at any time.

In another embodiment of the invention, the recesses are provided with ramps that provoke a noticeable snap-in effect.

This feature now provides the considerable advantage, under handling aspects, that the surgeon is told either by an audible clicking sound or by a noticeable movement of the fixing mechanism, whether or not the support has been fixed in its respective position.

In a further embodiment of the invention a special guide rail is provided to assist the introduction of the suturing aid into the wound area.

This feature provides the advantage that the suturing aid can be guided precisely along the guide and into and/or through the wound channel.

In a further embodiment of the invention the guide rail comprises a bent-off handle.

This feature provides the advantage that the guide rail can be easily held with the suturing aid applied.

In a further embodiment of the invention the guide rail comprises a guide groove for a guide pin at the distal end of the actuating element, which permits the depth of penetration of the suturing aid, relative to the depth of penetration of the guide rail, to be guided and controlled in a detectable fashion.

This feature provides the advantage to permit defined guiding and control during introduction of the suturing aid.

In a further embodiment of the invention the guide rail is provided with a graduation.

This feature provides the advantage that the depth of penetration of the guide rail can be monitored by means of the graduation. The depth of penetration of the trocar can be detected and felt, and the guide rail can then be pushed down to the desired depth. The latter depends on the particular properties of the patient's body. It is thus ensured that no organs will be damaged during introduction of the guide rail.

It is understood that the features mentioned above and those yet to be explained below can be used not only in the respective combinations indicated, but also in other combinations or in isolation, without leaving the context of the present invention.

The invention will be described in more detail and explained below with reference to certain selected exemplifying embodiments. In the drawings.

Figure 1:
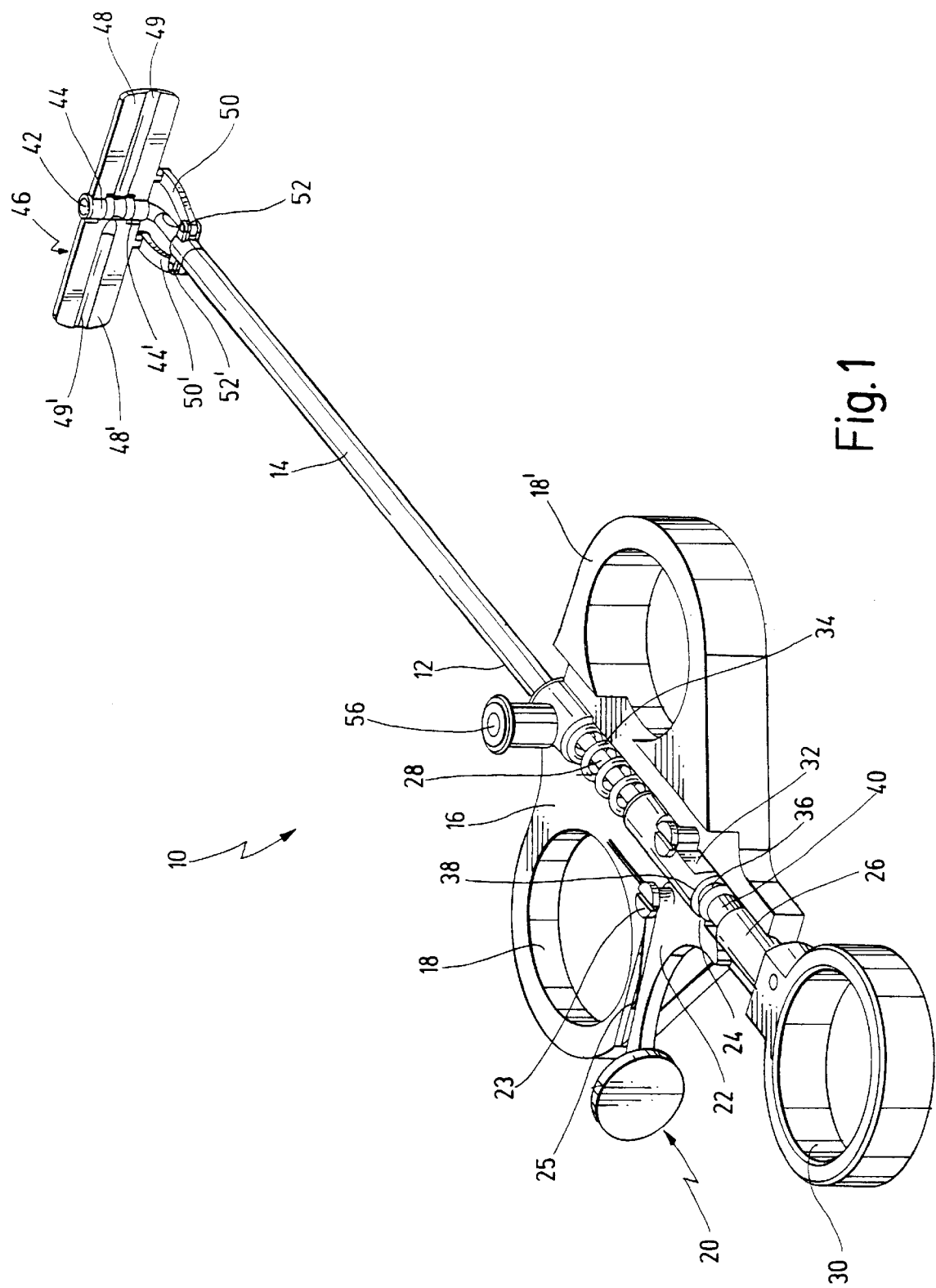
FIG. 1 shows a perspective view of a first embodiment of a suturing aid.

A first embodiment of a suturing aid, of which a perspective view is shown in FIG. 1, is indicated generally by reference numeral 10.

The suturing aid 10 comprises an elongated shaft 12 in the form of tube a 14.

The proximal end of the tube 14 is provided with a handle 16 which comprises two diametrically opposite, substantially annular finger rings 18, 18' extending in one plane.

The handle 16 is provided with a fixing mechanism 20, which comprises a spring lever 22.

The spring lever 22 is mounted to pivot about a stationary pivot axis 23 provided on the handle 16, and one of its ends carries a pin 24 arranged to engage corresponding recesses or grooves, in locking relationship, as will be described in more detail further below.

A spring 25 acts upon the spring lever 22 to urge it into its fixing and/or locking position. Mounted on the end of the spring lever 22, opposite the pin 24, is a key not specifically denominated, which can be actuated by a finger tip.

The tube 14 of the shaft 12 accommodates an actuating element 26 in the form of a rod 28 that can be displaced in lengthwise direction.

The rod 28 carries on its proximal end, projecting beyond the handle 18, a finger ring 30 which extends in the same plane as the finger rings 18, 18'.

The section of the rod 28 depicted in FIG. 1 is provided in its central portion, in the area of the handle 16, with a lateral flat portion 32 which serves on the one hand to protect the rod 28 against torsion in the tube 14, which effect is additionally achieved by corresponding clamping elements.

The flat portion provided diametrically opposite the flat portion 32, visible in FIG. 1, serves at the same time as sliding surface for the pin 24 of the spring lever 22, as will be described in more detail hereafter in connection with the description of the operation of the unit.

At a proximal distance from the flat portion 32, there is provided a first annular groove 36 whose flanks are configured as ramps 38.

The relatively narrow groove 36 is followed, proximally, by a relatively wide groove 40 whose flanks are likewise configured as ramps.

The pin 24 is configured in such a way that it can snap into both the groove 36 and the wide groove 40.

At its distal end, the rod 28 is provided with a bent-off end portion 42, which carries hinge-like joints 44 of a support 46.

The support 46 consists of two diametrically opposite, approximately rectangular vanes 48, 48', which are thus mounted to pivot about the bent-off end 42 of the rod 28. Correspondingly, the longitudinal center axis of the bent-off end portion 42 constitutes the joint axis 45 and the corresponding pivot axis of the vanes 48, 48'. On the side of the vanes 48, 48' that faces the proximal end of the suturing aid 10, there is provided a central guide groove 49, 49' extending along their longitudinal axes.

The vanes 48, 48' are pivotally joined with a flange 51 provided on the distal end of the shaft 12, via actuating levers 50, 50'. As will become apparent especially when regarded in conjunction with FIGS. 4 and 8, the actuating lever 50 is on the one hand pivotally joined with the flange 51, via a pivot shaft 52, and on the other hand pivotally joined with a lateral edge of the vane 48, via a pivot shaft 54. The spacing between the pivot axis 45 and the pivot shaft 54 is substantially equal to one third of the axial length of the vane 48. The same applies correspondingly to the joint between the vane 48' and the actuating lever 50'.

In the area of the handle 16, the shaft 12 is provided with a radially projecting connection piece 56 that serves for cleaning and scavenging the hollow shaft 12.

Figure 8:
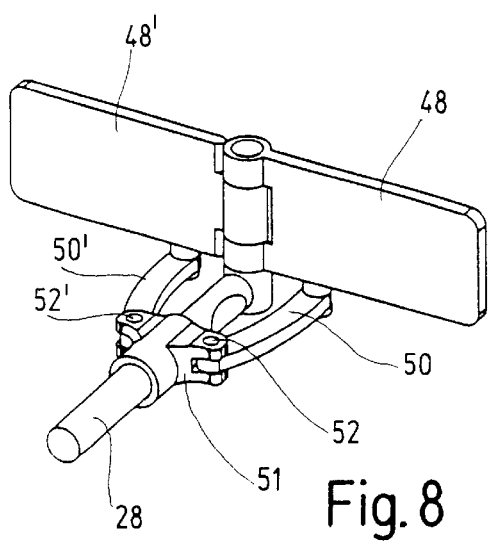
FIG. 8 shows a perspective view, corresponding to the representation of FIG. 4.
Figure 9:
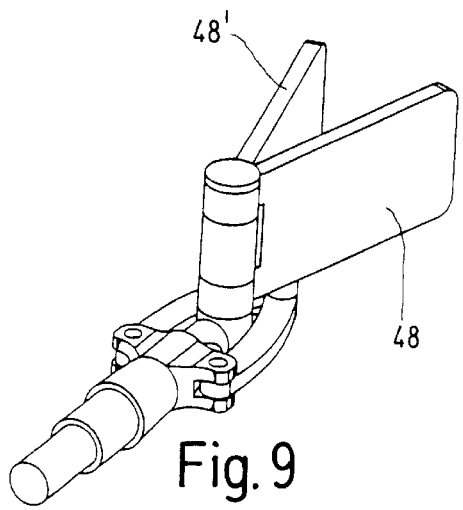
FIG. 9 shows a perspective view, corresponding to the representation of FIG. 5.

The different working positions and pivoted positions of the vanes 48, 48' will now be described with reference to the series of representations of FIGS. 2 to 5, and the series of representations of FIGS. 6 to 9 which show corresponding perspective views of the pivoted position of the vanes 48, 48':

The basic position of the vanes 48, 48', i.e. the position in which the suturing aid 10 is handed to the surgeon, is illustrated in FIG. 1 and FIG. 8. In this position, the vanes 48, 48' are swung out relative to the shaft axis by approximately 90° and extend in one and the same plane.

The pin 24 of the fixing mechanism 20 is engaged in the narrow groove 36 of the rod 28 in that position so that the vanes 48, 48' are immovably held in that angular position.

Figure 2:
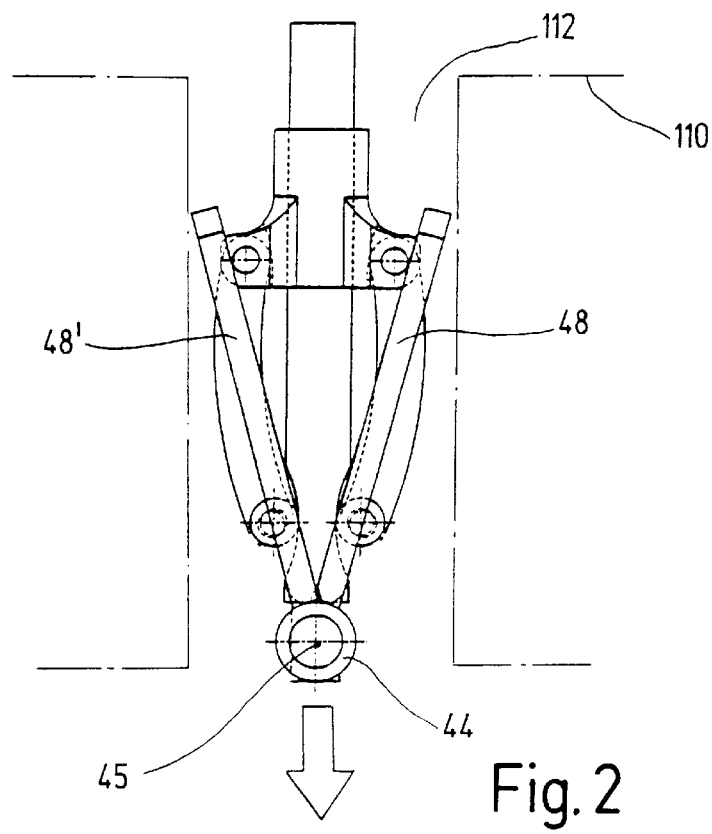
FIG. 2 shows a partly schematic view of the distal end portion of the suturing aid, with the support in its working position in which it is folded up towards the proximal end, as it is passed through a minilaparotomy.

Now, the surgeon grasps the suturing aid 10, and slides two fingers into the finger rings 18, 18', for example the index finger and the middle finger. The fixing mechanism 20 can now be released with the aid of the thumb, whereafter the suturing aid 10 can be inserted with its distal end first into a minilaparotomy 112, for example an abdominal wall 110, as illustrated in FIG. 2. The finger ring 30 need not be engaged for this purpose.

A process that facilitates this inserting action will be described hereafter with reference to FIGS. 11 to 14.

Figure 6:
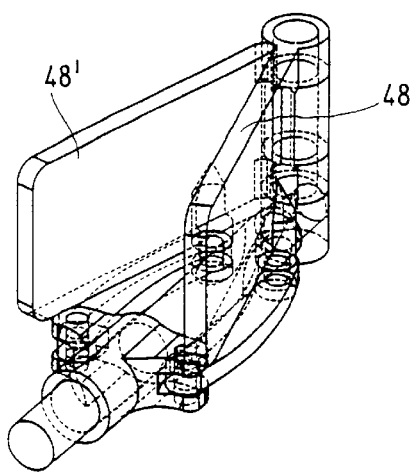
FIG. 6 shows a perspective view, viewed from the proximal towards the distal end, of the distal end portion of the suturing aid, in a position corresponding to the position of FIG. 2.
Figure 7:
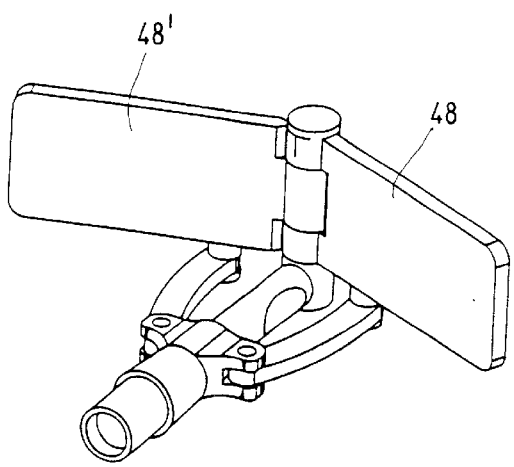
FIG. 7 shows a perspective view, corresponding to the representation of FIG. 3.

The diameter of the minilaparotomy 112 is considerably smaller than the radial extension of the folded-out vanes 48, 48', so that these are folded back towards the proximal end, thereby assuming a V-shaped position, as illustrated in FIGS. 2 and 6. This causes the rod 28 to move inside the shaft 12 towards its distal end, against the action of the spring 34, so that the finger ring 30 moves towards the handle 16. Although this motion may be supported by the surgeon it is performed automatically by the walls of the minilaparotomy 112, without any damage or dilatation of the minilaparotomy 112. The surgeon may therefore withdraw his thumb, for example, from the finger ring 30 during this process.

Figure 3:
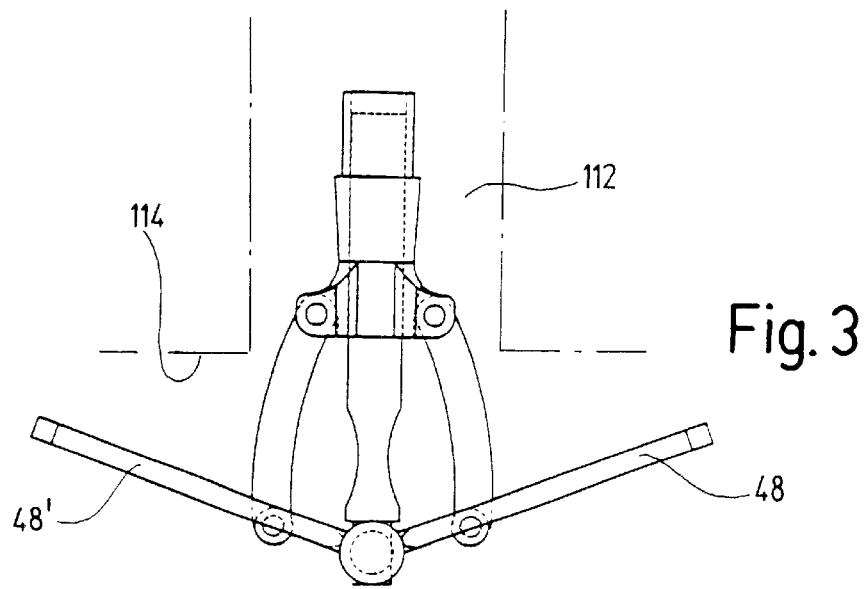
FIG. 3 shows a representation comparable to that shown in FIG. 2, but with the support in an intermediate position, already folded out laterally.

Once the distal end of the folded-up vanes 48, 48', with the V-shaped configuration, has passed the minilaparotomy 112, as is apparent from the transition between FIGS. 2 and 3, the force of the spring 34 comes to urge the rod 28 in the shaft towards its proximal end. Now, the vanes 48, 48' are swung out laterally, by means of the actuating lever 50, 50', until they assume substantially the intermediate position illustrated in FIG. 3. In this position, the pin 24 of the spring lever 22 of the fixing mechanism 20 has slid along the wide groove 40 and has come to abut against its distal flank, which is configured as a ramp.

The transition from the position shown in FIG. 2 to that shown in FIG. 3 is effected abruptly, under the action of the spring 22; this abrupt movement provokes a similarly abrupt movement of the finger ring 30 which tells the surgeon, or indicates, that the vanes 48, 48' have passed the minilaparotomy 112 and have entered the free abdominal cavity.

Figure 4:
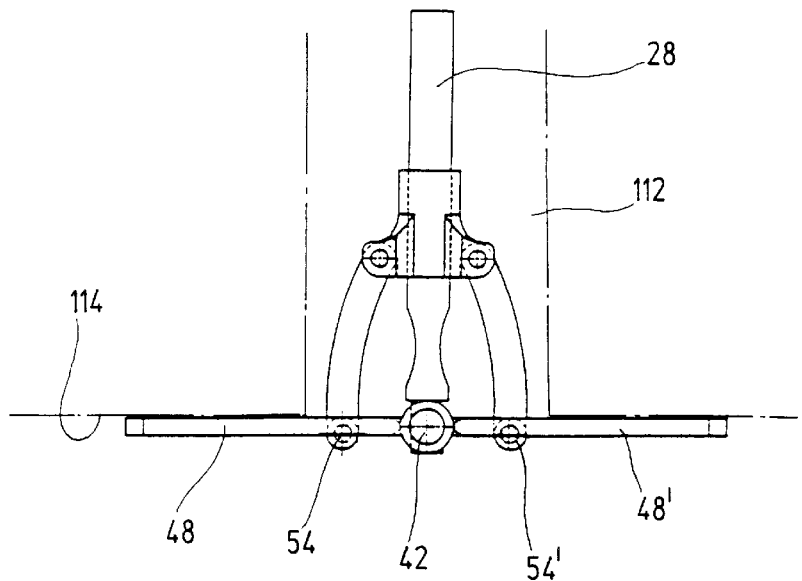
FIG. 4 shows a representation comparable to those of FIGS. 2 and 3, with the support in a working position in which it is fully folded out laterally.
Figure 5:
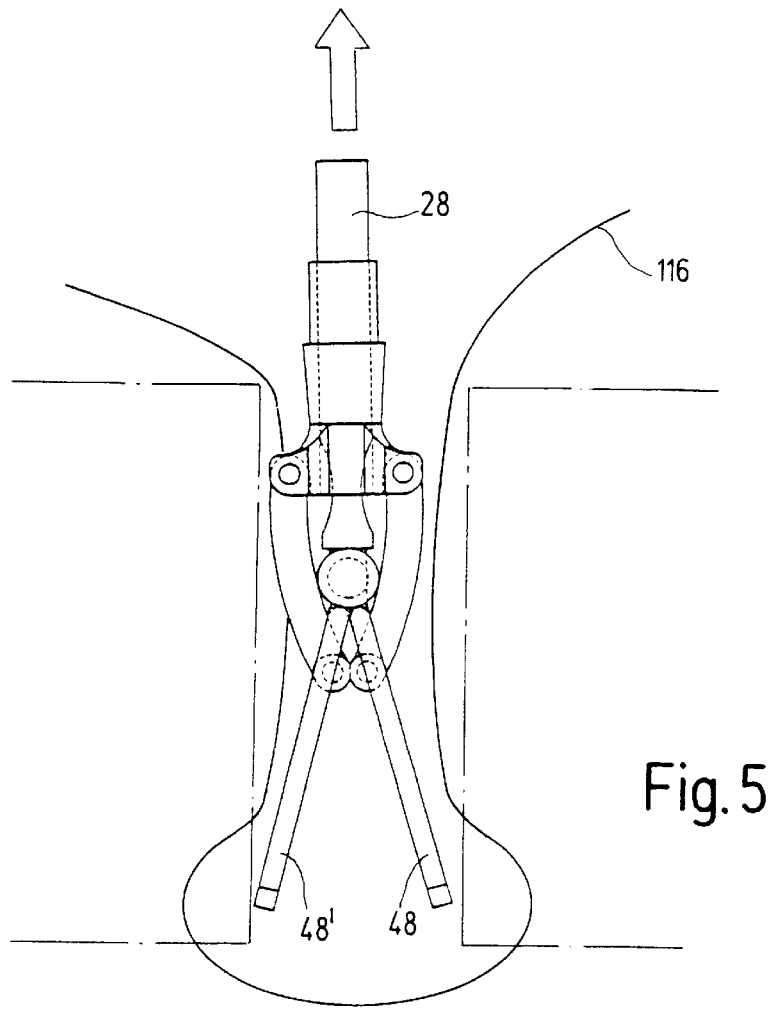
FIG. 5 shows a representation comparable to those of FIGS. 2 and 4, with the support in a working position folded out towards the distal end, as it is pulled back from a minilaparotomy.
Figure 10:
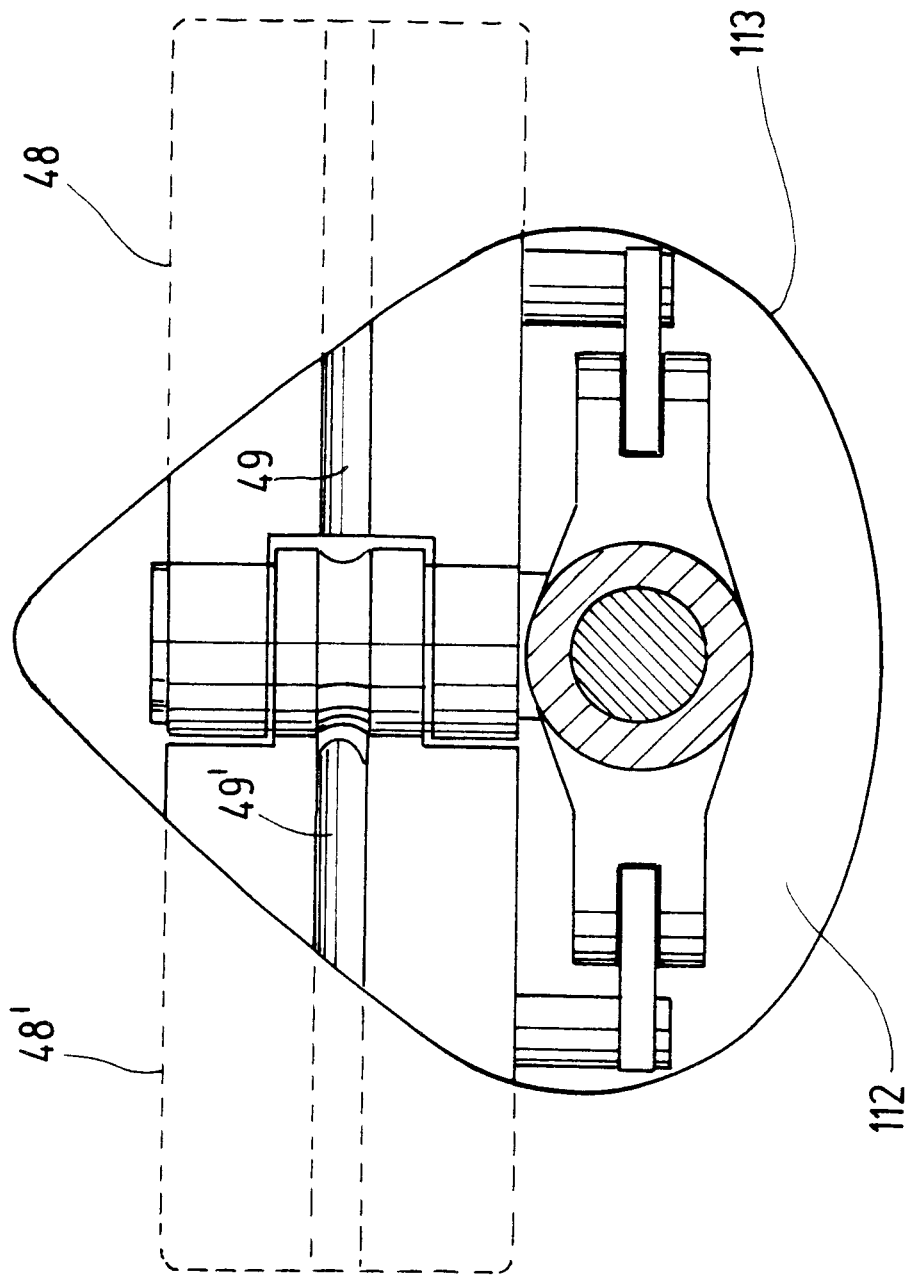
FIG. 10 shows a top view, viewed from the proximal towards the distal end, of a minilaparotomy, with the suturing aid already inserted and occupying the extended position shown in FIG. 4.

The surgeon then pulls back the suturing aid 10 by a small amount, thereby applying the vanes 48, 48' against the lower face 114 of the abdominal wall 110, as illustrated in FIG. 4. During the transition from the pivoted position illustrated in FIG. 3 to that illustrated in FIG. 4, the pin 24 passes over the flank and/or the ramp of the groove 40 and drops back into the groove 36. The surgeon sees the minilaparotomy 112 from its outside, as illustrated in FIG. 10. He can now introduce from the outside a tool with a thread, for example a Dechamps hook, whose end exhibits a corkscrew-like shape, and can apply sutures and/or a thread 116, as indicated in FIG. 5. The orientation of the suturing device is assisted by guide grooves 49, 49', provided on the vanes 48, 48' which, for the sake of clarity, are depicted only in FIGS. 1 and 10. Once the Dechamps hook has hit upon the vane 48 and/or the vane 48', it can be displaced a little until it engages the groove 49 or 49'. The suturing device can now be properly aligned, and the surgeon can apply the thread 116 on both sides of the shaft, as indicated in FIG. 5.

After the thread 116 has been applied, the fixing mechanism 20 is released, and the rod 28 is pulled towards the proximal end with the aid of the thumb engaging the finger ring 30.

The actuating levers 50, 50' now push the vanes 48, 48' in downward direction, in the view of FIG. 5, so that they are folded down towards the distal end of the unit to assume a V-shaped position as illustrated in FIG. 5. Folding down the vanes further is neither necessary nor desirable in order to exclude that tissue parts may get caught between the folded-down vanes 48, 48'.

The pin 24 of the fixing mechanism now slides along the flat portion 32 of the rod 28.

In the position shown in FIG. 5, the suturing aid 10 can then be pulled off the minilaparotomy 112 and the body without any difficulty.

Finally, the thread 116 can be knotted to close the minilaparotomy.

Figure 11:
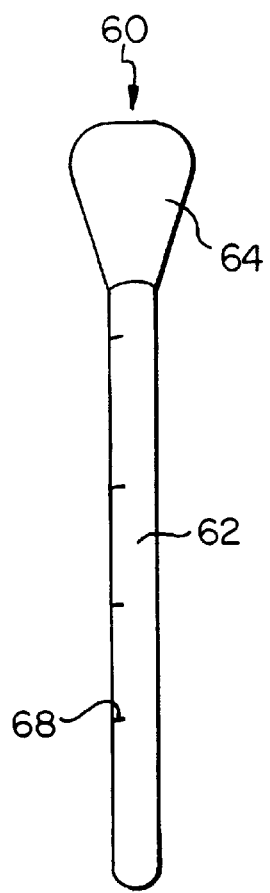
FIG. 11 shows a side view of a guide rail intended for inserting the suturing aid into the minilaparotomy.

A guide rail 60, as shown in FIG. 11, is provided in order to facilitate the application of the suturing aid 10 and its insertion into the minilaparotomy 112.

Figure 12:
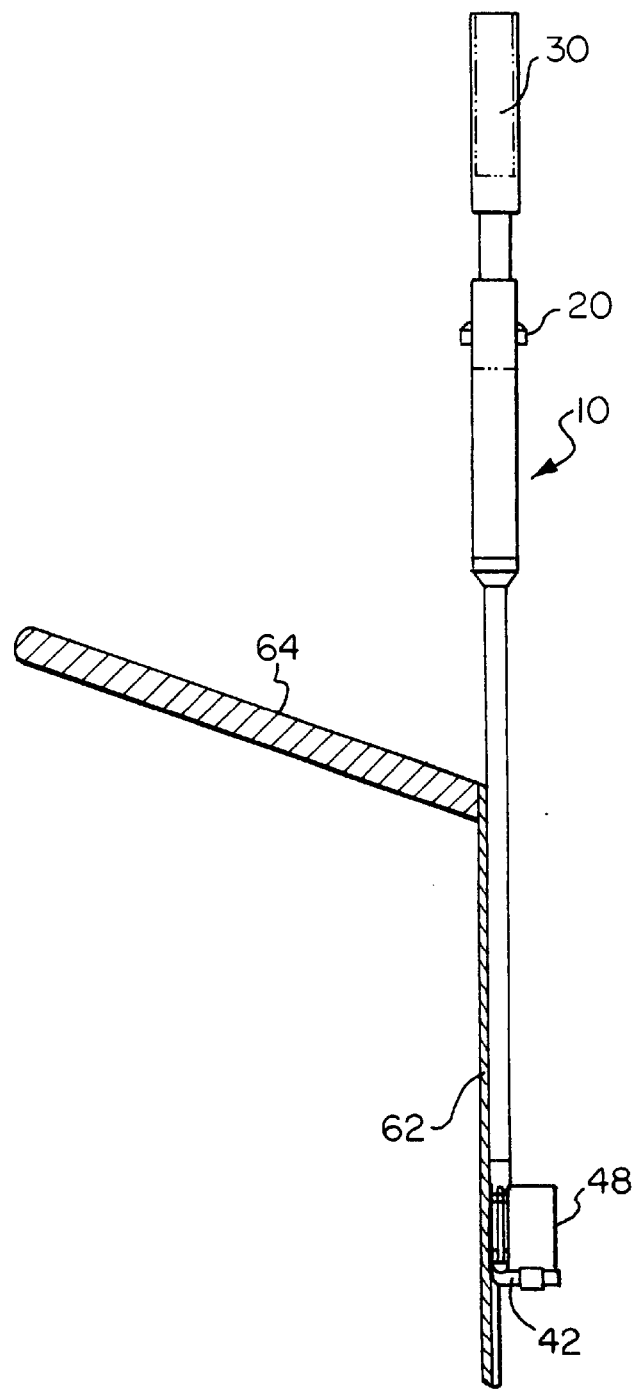
FIG. 12 shows a side view of the guide rail of FIG. 11, turned by 90°, with the suturing aid according to FIG. 1 applied.

The guide rail 60 comprises a guide groove 62, to which the suturing aid 10 can be applied in the manner shown in FIG. 12.

The guide rail 60 comprises a bent-off handle 64 so that both units, i.e. the guide rail 60 and the suturing aid 10, can be held by different hands, without disturbing one another. The guide rail 60 is provided with a graduation 68 by means of which the depth of penetration can be read.

Figure 13:
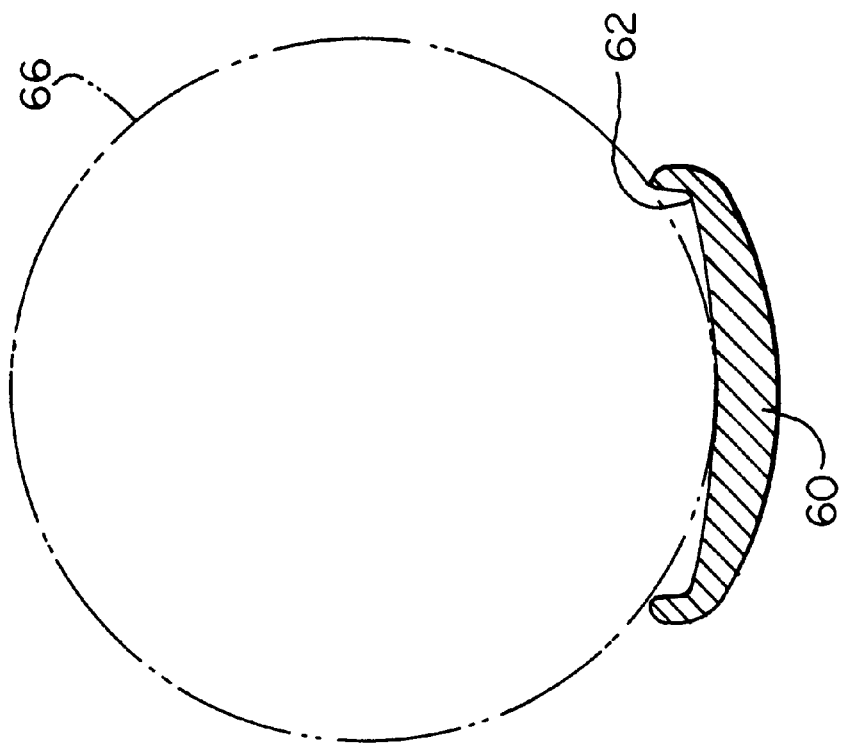
FIG. 13 shows a cross-sectional view of the guide groove of the guide rail according to FIG. 11, in grossly enlarged scale, with the guide rail applied to a trocar.
Figure 15:
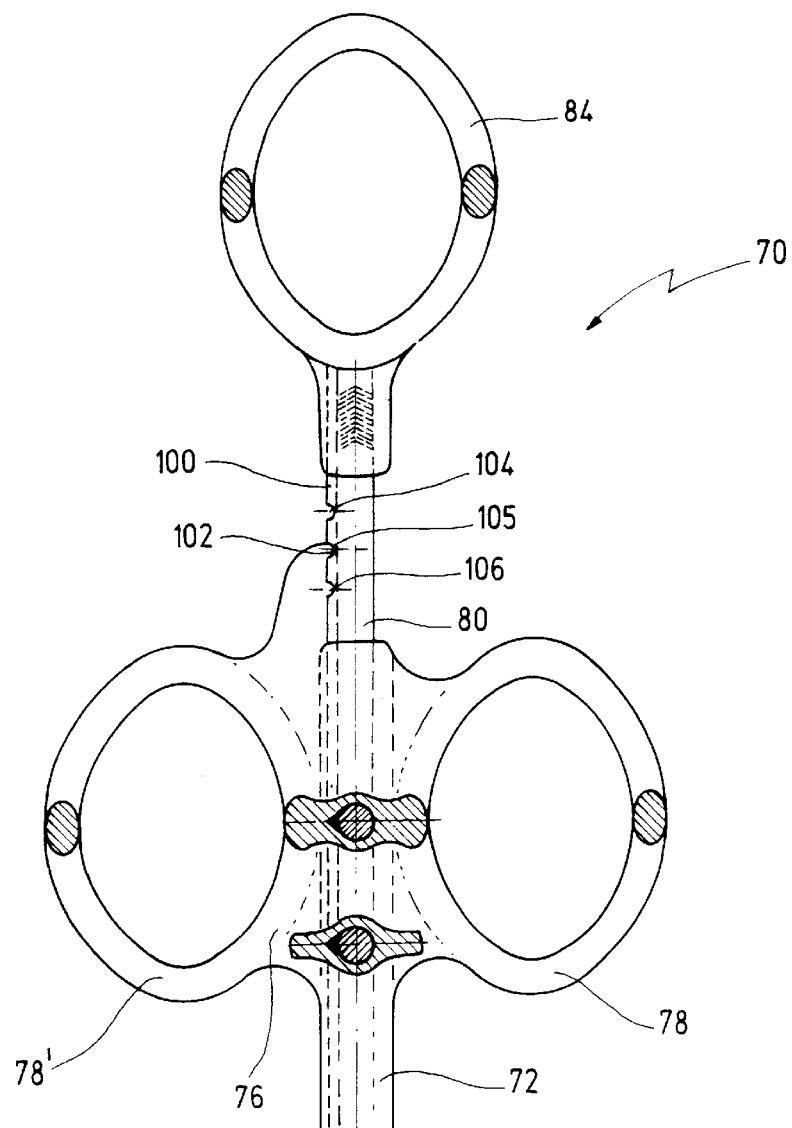
FIG. 15 shows a side view of another embodiment of a suturing aid, made from plastic materials.
Figure 16:
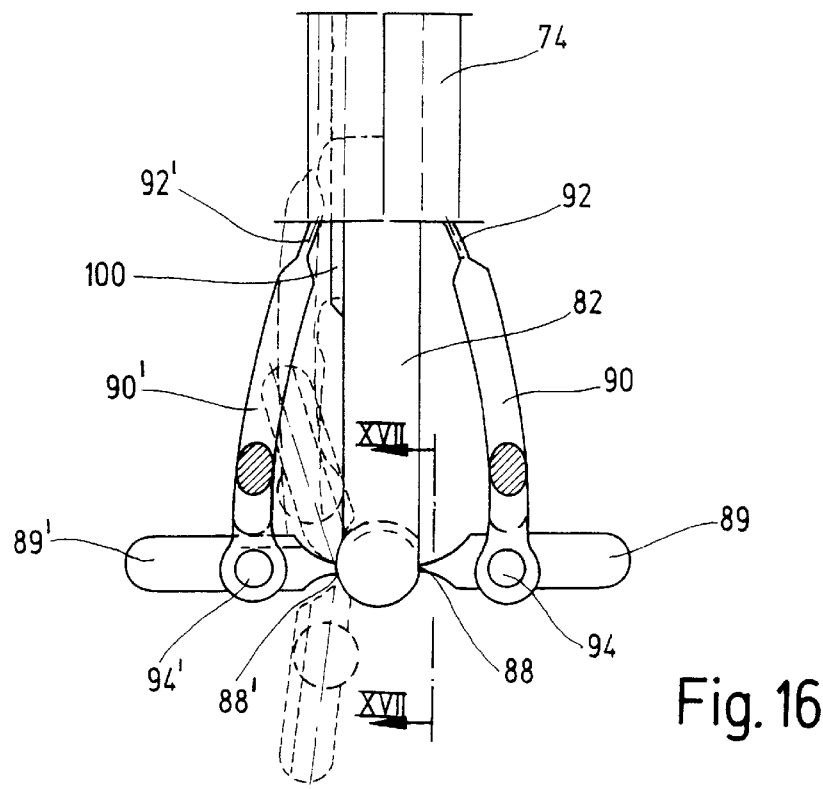
FIG. 16 shows an enlarged representation of the suturing aid of FIG. 15, in the distal area.
Figure 17:
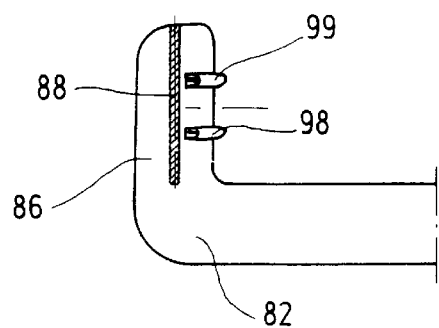
FIG. 17 shows a sectional view, along line XVII—XVII in FIG. 16.

From the enlarged cross-sectional view of FIG. 13 it appears that the guide groove 62 exhibits a special cross-sectional profile.

This cross-sectional profile is configured in such a way that the guide rail 60 can be introduced into the body along a trocar, as indicated by the contour line 66 in FIG. 13.

Figure 14:
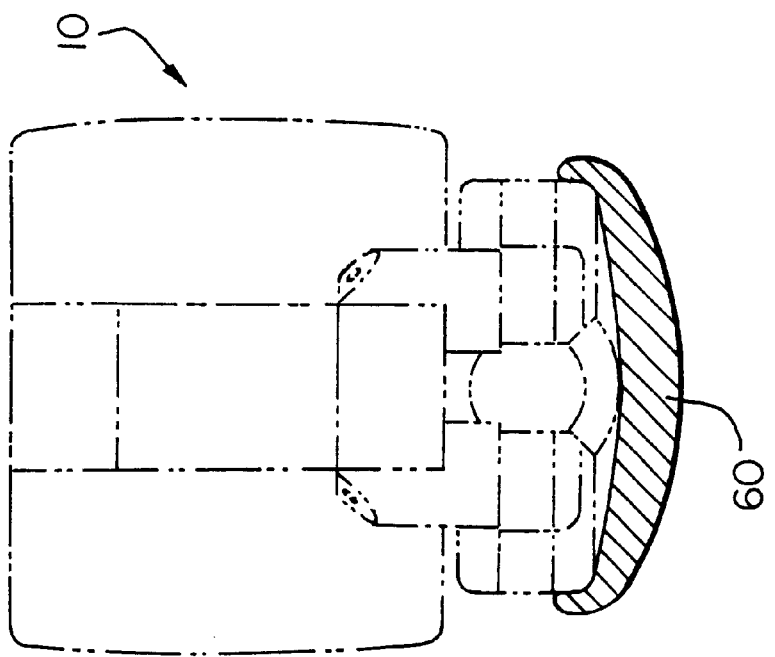
FIG. 14 shows a sectional view comparable to that of FIG. 13, with the suturing aid applied.

After insertion of the guide rail 60, during which process the depth of penetration can be monitored via the graduation 68, the trocar is pulled off. Then the suturing aid 10 is applied on the guide groove 62, as illustrated in FIGS. 12 and 14, and inserted into the body and through the minilaparotomy 112. This auxiliary device ensures easy handling, especially the automatic application and insertion of the suturing aid 10.

The suturing aid 10 described above is fully made from metal so that it can be used several times, being suited for sterilization in an autoclave.

FIGS. 15 to 18 show a further embodiment of a suturing aid according to the invention, indicated generally by reference numeral 70.

The suturing aid 70 exhibits generally the same configuration as the suturing aid 10, but is fully made from plastic materials, especially from molded plastic parts, which means that it can be produced at lesser cost and can be used as single-use unit.

Correspondingly, the suturing aid 70 comprises a shaft 72 in the form of a tube 74. The proximal end of the tube 74 is provided with a handle 76 carrying two finger rings 78, 78'.

Accommodated in the tube 74 is an actuating element 80 in the form of a rod 82 that can be displaced in lengthwise direction and carries a finger ring 84 on its proximal end.

At its distal end, the rod 82 comprises a bent-off end portion 86 (see especially FIG. 17) with the lateral vanes 89, 89' integrally molded thereon, via flexible plastic bridges 88, 88'.

Accordingly, the flexible plastic bridges 88, 88' act as film hinges. Both actuating levers 90, 90' are hinged on the distal end of the tube 74 via plastic bridges 92, 92' (see especially FIG. 16). At the opposite end, the actuating levers 90, 90' are clipped into projections 94, 94' in the form of hinge shafts provided on the lateral edges of the vanes 89, 89'.

Figure 18:
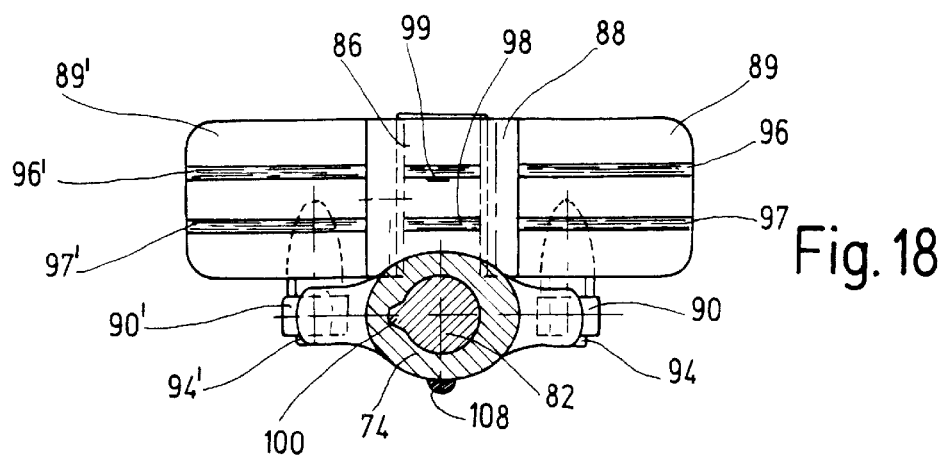
FIG. 18 shows a representation, comparable to the sectional view of FIG. 10, of the suturing aid in laterally folded-out condition.

As can be seen best in the representation of FIG. 18, the vanes 89, 89' are provided with two lengthwise extending guide grooves 96, 97 and 96', 97', respectively.

Likewise, the bent-off end portion 86 of the rod 82 is provided with correspondingly positioned guide grooves 98, 99 so as to provide a continuous guide. A rib 100 extending along the outside of the rod 82 is molded integrally with the latter.

The tube 74 has a corresponding inner contour, as can be seen best in the sectional view of FIG. 18, so that the rod 82 is secured against torsion in the tube 94.

At the proximal end, before the finger ring 84, the rib 100 is provided with recesses 104, 105, 106, for elastically receiving and releasing a corresponding knob on the handle 76, for which purpose the recesses are provided with corresponding entry and exit slopes. The three recesses 104, 105, 106 indicate/correspond to the three working positions; accordingly the knob 102 engages, in the representation of Fig. 15 the middle recess 105 which indicates that it occupies the working position in which the vanes 89, 89' are folded out laterally at approximately a right angle. As the described design does not require a spring to act upon the rod, the vanes 89, 89' are moved into the corresponding folded-up or folded-down positions via the finger ring 84, whereby the knob 102 is caused to engage the corresponding recess 104 or 106, respectively.

The distal end portion of the Act el 74 is provided with a radially projecting pin 108-that can be fitted in a corresponding groove in a guide rail in order to achieve defined insertion of the suturing aid 70.

What is claimed is:

1. A suturing aid for closing minilaparotomies from minimal-invasive surgical operations, comprising a shaft having a distal end and a proximal end, said distal end of said shaft is provided with at least one plane support that is swung out laterally from said shaft, and an actuating element for swinging out said support wherein said support is moved via said actuating element between a first working position having folded up said support towards said proximal end to substantially adjacent said shaft for inserting said suturing aid into said minilaparotomy, a second working position having folded out laterally said support for supporting a suture performance, and a third working position having folded down said support towards said distal end of said shaft for pulling off said suturing aid from said minilaparotomy.

2. The suturing aid of claim 1, wherein said plane support comprises two diametrically opposite vanes.

3. The suturing aid of claim 1, wherein said actuating element is configured as a rod, which is arranged to slide along said shaft and is hinged, on its distal end, on said support, with an axis of said hinge forming a pivot axis of said support.

4. The suturing aid of claim 3, wherein said support is hinged, at a certain distance of its pivot axis, on one end of an actuating lever, whose other end is hinged on said shaft.

5. The suturing aid of claim 4, wherein a distance between said pivot axis of said support and the connection point of said lever corresponds to approximately one third of an overall length of said support.

6. The suturing aid of claim 1, wherein at least one guide for guiding a suturing tool is provided on a side of said support facing said proximal end of said shaft.

7. The suturing aid of claim 1, wherein said actuating element is disposed within said shaft and is prohibited of turning inside said shaft.

8. The suturing aid of claim 1, wherein said actuating element is biased by a spring in such a way that said support is moved automatically from its first working position having folded up said support towards said proximal end of said shaft to its second laterally folded-out working position.

9. The suturing aid of claim 8, wherein a force of said spring is adjusted in such a way that said support will be folded out laterally only to an intermediate position somewhat before reaching the second working position in which said support is fully folded out laterally.

10. The suturing aid of claim 1, wherein said shaft is provided with orientation marks indicating an actual working position of said support.

11. The suturing aid of claim 1, wherein said actuating element is provided with orientation marks indicating a particular working position of said support.

12. The suturing aid of claim 1, wherein said shaft and said actuating element are provided with orientation marks indicating an actual working position of said support.

13. The suturing aid of claim 1, wherein a fixing mechanism is provided by means of which said support can be locked in any of said working positions.

14. The suturing aid of claim 13, wherein said fixing mechanism is configured as a spring lever, pivoted on said shaft, which spring lever comprises a locking element arranged to engage corresponding recesses provided on said actuating element.

15. The suturing aid of claim 14, wherein said recesses are provided with ramps that provoke a noticeable snap-in effect.

16. The suturing aid of claim 1, wherein a guide rail is provided for assisting an introduction of said suturing aid into said minilaparotomy.

17. The suturing aid of claim 16, wherein said guide rail comprising a guide groove for a guide pin provided at a distal end of said actuating element, which allows a depth of penetration of the suturing aid, relative to a depth of penetration of said guide rail to be guided and controlled in a detectable fashion.

18. The suturing aid of claim 17, wherein said guide rail is provided with a graduation.

19. The suturing aid of claim 18, wherein the guide rail comprises a bent-off handle.

* * * * *